United States Patent
Balch et al.

(10) Patent No.: US 12,026,205 B2
(45) Date of Patent: Jul. 2, 2024

(54) META-ANALYSIS METHODS FOR MULTI-THERAPEUTIC CONTEXT-SPECIFIC DOMAINS

(71) Applicant: Carla Wood Balch, Memphis, TN (US)

(72) Inventors: Carla Wood Balch, Memphis, TN (US); Tim Fitzgerald, Colorado Springs, CO (US); William Pretsch, Memphis, TN (US)

(73) Assignee: Carla Wood Balch, Memphis, TN (US)

( * ) Notice: Subject to any disclaimer, the term of this patent is extended or adjusted under 35 U.S.C. 154(b) by 0 days.

(21) Appl. No.: 17/918,717

(22) PCT Filed: Apr. 19, 2021

(86) PCT No.: PCT/US2021/028005
§ 371 (c)(1),
(2) Date: Oct. 13, 2022

(87) PCT Pub. No.: WO2021/212117
PCT Pub. Date: Oct. 21, 2021

(65) Prior Publication Data
US 2023/0244722 A1 Aug. 3, 2023

Related U.S. Application Data

(60) Provisional application No. 63/011,771, filed on Apr. 17, 2020.

(51) Int. Cl.
*G06F 16/906* (2019.01)
(52) U.S. Cl.
CPC .................. *G06F 16/906* (2019.01)

(58) Field of Classification Search
CPC ...... G06F 16/906; G16H 50/70; G16H 70/20; G16H 10/60
See application file for complete search history.

(56) References Cited

U.S. PATENT DOCUMENTS 6,460,024 B1 10/2002 Smith
8,731,966 B2 5/2014 Breitenstein et al.
(Continued)

OTHER PUBLICATIONS

European Application No. 21788200 Supplementary Search Report dated Mar. 27, 2024, 7 pages.

*Primary Examiner* — Mark D Featherstone
*Assistant Examiner* — Kweku William Halm
(74) *Attorney, Agent, or Firm* — Boyle Fredrickson S.C.

(57) ABSTRACT

The described platform's infrastructure transforms domain-specific data into unique graphic component parts (a shape), providing a visual graph representation of the current status of the domain data. The software on the platform provides instructions to allow users to manipulate the domain-specific data and shapes. The domain-specific information may be used in hypothesis generation, prioritization among domains, decision support, and domain modeling over a time period. The platform enables industry contributors and consumers to collaborate using all the domains. The domain-specific shape is created then used by Platform Machine Vision, enabling time-saving decision support across all domains and industries. Additional benefit of creating each domain shape is the shapes may be combined for an Overall Graphic, which is a new kind of visual representation across domains. The Overall Graphic is a portable industry status.

23 Claims, 11 Drawing Sheets

(56) References Cited

U.S. PATENT DOCUMENTS

| | | | |
|---|---|---|---|
| 2006/0136259 A1* | 6/2006 | Weiner | G16H 50/70 |
| | | | 705/2 |
| 2007/0118399 A1* | 5/2007 | Avinash | G16H 40/20 |
| | | | 705/2 |
| 2010/0114899 A1 | 5/2010 | Guha et al. | |
| 2011/0242108 A1 | 10/2011 | Mital et al. | |
| 2011/0261049 A1* | 10/2011 | Cardno | G06Q 40/04 |
| | | | 345/419 |
| 2011/0295783 A1 | 12/2011 | Zhao et al. | |
| 2012/0136676 A1 | 5/2012 | Goodall et al. | |
| 2014/0325643 A1 | 10/2014 | Bart | |
| 2017/0161613 A1* | 6/2017 | Dubey | G06N 20/00 |
| 2019/0215338 A1* | 7/2019 | Baggeroer | G06Q 10/06316 |

\* cited by examiner

META-ANALYSIS METHODS FOR MULTI-THERAPEUTIC CONTEXT-SPECIFIC DOMAINS

CROSS-REFERENCE TO RELATED APPLICATION

The present application claims priority from U.S. Provisional Pat. App. No. 63/011,771, filed Apr. 17, 2020, which is incorporated herein by reference as if set forth in full below.

BACKGROUND OF THE INVENTION

I. Field of the Invention

The present inventive subject matter relates to collecting, recognizing, stratifying, organizing and manipulating industry data. The Industry Platform infrastructure utilizes image recognition in conjunction with computing technologies associated with data ingestion, data normalization, analytics, data-created plots or graphs. The data and images ingested include multiple domains specific to scientific, historical, scientific, technologic, business and socioeconomic. The platform has the ability to transform domain text data to a standardized graphic representation, a shape. It is contemplated that various domain data will take on unique standardized graphic representations. The platform will read, via machine vision, the plurality of industry domain-specific shapes. The platform may trigger computer-based domain-specific actions based on prioritization of a particular domain (e.g., Domain 1—historic, Domain 2-scientific, Domain 3—socioeconomic) by a platform user. Please note, the accompanying figures illustrate domain-specific shapes as circles and combined domain graphic, Overall Graphic as a rectangle. These shapes are chosen for illustration purposes. Actual shapes generated by the platform may be different.

II. General Background

The background description includes information that may be useful in understanding the present inventive subject matter. It is not an admission that any of the information provided herein is prior art or applicant admitted prior art, or relevant to the presently claimed inventive subject matter, or that any publication specifically or implicitly referenced is prior art or applicant admitted prior art.

Scientific studies are being conducted and results published with increasing velocity. The discoveries are important to Industry Contributors and Consumers 100, 132, 134 for many reasons. These publications display graphics and figures that are difficult to discern. Industry decisions are often made by executives based on a limited set of information (e.g. a test result, a map) without an overarching view of all available credible publications, complete domain history, scientific information, social determinants of impact, public preferences and government policy limitations that may affect a plan of action. An industry decision made without all real-time information is likely less than optimal.

An example from healthcare, electronic medical records (EMR) began clinical decision support methodologies in mid-2000s. The goal for these algorithm-based alerts for clinicians was to ensure a treatment was considered and administered according to appropriate regulatory guidance. The algorithms were based on "if/then statements" using unique data fields in the EMR. The approach was sufficient for each EMR used by clinicians treating one patient. However, the advent of sophisticated, complex and data-dense scientific diagnostics that are part of clinical decision support renders the old algorithmic-based decision support clunky and slow.

The background of the unique technological advance included herein is based on the adage "a picture tells a thousand words". From a decision-making perspective, scientific or sophisticated domain data combined with standardized graphic formats for other domain-specific information should be read with machine vision to provide faster, more complete and more inclusive real-time information to decision-makers. Approaching decision-making in this manner ensures the target scenario is put into context, as much as possible, regarding all aspects for an optimal outcome.

The need for the platform in healthcare is urgent. Over 15 million patients live with cancer in the US. Additionally, 25 m patients suffer with rare diseases. Molecular diagnostics figure heavily in optimized outcomes for these patients. Unless each patient's treatment decision and non-clinical decisions are made with full context, society will not see significant improvements in outcomes for these vulnerable populations.

Similarly, pharmaceutical companies developing innovative treatments require this same broad context-based real-time capability to improve new drug development, stratification of patients and measure outcomes. It is contemplated that this platform and inventions references herein are useful beyond cancer and rare diseases.

While patients are industry consumers, currently patients are generally not major decision-makers regarding treatment, supportive care, and socioeconomic-related choices. The platform will combine and standardize hard-to-understand information across domains and make available to patient users as a means to collaborate in industry decisions with other parties.

SUMMARY OF THE INVENTION

Considering the virtuous cycle of industry contributors and industry consumers, the inventive platform and technology described herein is accessed by internet, updated regularly with refreshed meta-analysis of each domain. The technology components move away from unique data field-driven algorithms to a visual machine vision assessment of complex data from across multiple domains. The domain information is ingested from publicly available data sources, contracted data sources and knowledge bases. This data includes scientific publications and articles with results, digital images from research, speech or voice recordings of domain-specific presentations. In addition to publicly available information, the platform directly ingests industry-specific information in a secure manner from industry providers' technology solutions with appropriate consent. Certain embodiments of the present invention include industry applications, industry contributors and consumers but are not limited to industry decisions. Other industries with similar needs to make decisions or create hypotheses across relevant domains may benefit from the invention. For example, security platforms may use domain-specific standardized graphics to represent massive amounts of sophisticated population data and travel data in order to make decisions about security protocols.

In accordance with one embodiment, the present invention is a server or device including one or more of the following: (1) executable software instructions where software instructions interact with data or images from the databases, domain plotter, descriptor(s), parse relevant data into unique data fields, align data into domain database(s) (i.e. Domain Cylinder), which are informed by software instructions to generate transformed domain-specific shape(s), a visual representation of unique data from a domain, which upon prioritization generates at least one suggestion for action, where suggested action may trigger a transaction (e.g. a comparison of domain graphics over time or analysis of domain graphics with hypothetical interventions applied to the domain or overall graphic), and suggested actions may be calculated from a domain meta-analysis data or across multiple domain meta-analyses; (2) a database, interfaces to industry databases, processor, computer readable memory storage, data ingestion capabilities (e.g. ETL, SFTP), Optical Character Recognition (OCR) capabilities, Natural Language Processing (NLP) capabilities, speech recognition capabilities, data evaluation (e.g. Context-Specific Domain evaluation capability) to determine a certain context for incoming information, data categorization (e.g. Context-Specific Domain tagging capabilities) to tag data into specific domains (e.g. Domain 1, Domain 2, Domain 3), a graphic generation capability (e.g. Domain Plotter) to plot points or generate graphics using data in categorized domains; (3) image recognition capabilities, image ingestion capabilities (e.g. ETL, SFTP), Optical Character Recognition (OCR) capabilities, image recognition capabilities (e.g. custom visual parsers, or discrete cosine transform (DCT) image compression algorithm), graphic evaluation (e.g. Context-Specific Domain evaluation capability) to determine a certain graph or chart style for incoming information (e.g. line, bar, network, pie), image categorization (e.g. Context-Specific Domain tagging capabilities) to tag a graphic into specific domains, a graphic generation capability (e.g. Domain Plotter) to plot points or generate graphics using data in categorized domains. A database or reference library of analytical graph styles (e.g. bar, line, scatterplot, waterfall, circle, pie, histogram, gauge and area graphs). Wherein the data ingestion interface may include one or more of the following: camera, scanner or optical sensor, voice recording, Application Programming Interface (API), Extraction, Transformation and Load process (ETL), Secure File Transfer Protocol (SFTP). Said embodiment may be able to recognize data and graphics as a Domain type and tag as a Domain (e.g. financial, scientific, operational), deconstruct data and images of an individual or group belonging to a domain to generate a new standardized domain shape, which represents the scenario of the individual or group of the domain, domain-specific data, transformed or not, is added regularly to domain-specific Domain Cylinder.

In another embodiment, the invention comprises a computer readable medium storing at least one graphic (either ingested or created by unique data) and software instructions that cause a processor to perform operations comprising: obtaining a graphic or plot, or unique data from which a graphic can be created, which represents a individual, group of individuals or domains; detecting data or graphic for Domain tag; converting the data or graphic (including a generated standardized graphic) for meta-analysis and; associating structured data and graphic with an ideal representation of statistical methods or visual plot generation assigned to each Domain; and initiating a transaction involving at least one device based on the descriptor.

In another embodiment, the invention comprises a computer readable medium storing at least one graphic (either ingested or created by unique data) and software instructions that cause a processor to perform operations comprising: obtaining a graphic or plot, or unique data from which a graphic can be created, which represents an individual, group of individuals or domains; detecting data or graphic for Domain tag; converting the data or graphic (including a generated standardized graphic) for meta-analysis and; associating structured data and graphic with an ideal representation of statistical methods or visual plot generation assigned to each Domain; and initiating a transaction involving at least one device based on the descriptor.

In the context of the foregoing, the representation may comprise a set of data, aggregated data, industry-specific data or publicly available data, scientific articles and graphs, or non-public data ingested directly to server. The descriptor may comprise domain-specific set of data, aggregated data, industry-specific data or publicly available data, scientific articles and graphs, or non-public data ingested directly to server. Meta-analysis in each Domain Cylinder may be performed regularly and stored in the domain-specific Domain Cylinder. Each Domain may have an ideal meta-analysis methodology and corresponding graphic output, that may be the same or different across domains. Domain-specific meta-analysis may be available for reference as machine vision reads domain shapes. Software may use the model of the Steinmetz Plot to combine Domain Cylinders, full of domain-specific data and images, refreshed from data ingestion regularly, and Domain Cylinders may display a date of last ingested data, graphic or meta-analysis. Machine vision can be used to read arranged domain shapes to allow unique domain shapes to compare, contrast, summarize domain shape to each other or historical domain shapes and meta-analyses.

In the above referenced embodiments, Intervention Candidate(s) are potential actions related to a Domain. The instructions for Machine Vision may direct the addition, removal or change of a specific data point or set of data points to visually display the potential scenario outcome. Each Intervention Candidate(s) Machine Vision read is uniquely stamped and available for user to review or trigger transactions (e.g. deploy resources to a disaster zone). Further, the invention may insert domain-specific Intervention Candidate(s) standardized shapes or data into machine vision of domain shapes to expand or refine overall understanding of domain scenarios and potential outcomes.

In the above referenced embodiments, the invention may prioritize concepts within a domain, or across domains which initiates machine vision weight specific domain scenarios for decision making suggestions. The prioritized preferences by a user is a digital transaction comprised of at least one of the following: a Domain 1 transaction, Domain 2 transaction, Domain 3 transaction (e.g. financial transaction, a database query, a list of interventional options, list of available options, an insurance transaction, a notification or software user-specific alert, a technology transaction (including Artificial Intelligence or Machine Learning), a Health Insurance Portability and Accountability Act (HIPPA), or security transaction). Presentation of domain-specific or aggregated decision support results may include text, generated graphic or utility graphic (e.g., bar code or QR code). The decision support transaction includes displaying a report, or a software with decision support options, a software link to workflow automation, a software link to analytics available for viewing or manipulation by the user of the software. Selected decision support action triggers workflow automation within the domain or across domains for a total scenario transaction. Records decision and adds scenario to the domain specific database. Temporal Changes for hypothesis generation within domain and across domains are available. Temporal Changes may be added to meta-analyses if outcomes of specific interventions are captured and become part of the Domain Cylinder.

In the above referenced embodiments, the invention may utilize machine vision to read and summarize domain-specific and multi-domain shapes to create an Overall Graphic, a display of the current status of the individual or group. A perimeter or outer track of a shape (e.g. rectangle) is plotted with data points represented by shapes, sizes, colors in segments within the outer track of the Overall Graphic shape. The perimeter or outer track of the Overall Graphic displays the status of the individual or group being investigated. The interior of the shape, internal space remaining inside the perimeter's outer track plots and displays points of the individual or group being investigated as compared to the known universe. The comparison may be limited to similar individuals or groups. The comparison data for plotting the interior graph requires the relative positions of individual or group to the corresponding data element in the known universe, which is generated by and includes all data and meta-analyses of from the Domain Cylinders.

In the above referenced embodiments, the invention may utilize machine vision to read Overall Graphics across timepoints. Each generated Overall Graphic has a discrete time stamp. Each Overall Graphic has a demographic description of the assumptions, prioritized selections or intervention candidate(s) applied. The various embodiments may have the ability to play a time lapse video of Overall Graphic or individual Domain shapes is stored in the server.

In the above referenced embodiments, the invention may comprise a platform available to Consumers and Contributors via web-based connection to Server with appropriate security and permissions. Platform includes data, graphics, transformed Domain Shapes, Overall Graphics, Intervention Candidates, Decision Support Priority Settings, Decision Support transactions and outcomes, up-to-date Domain Meta-analyses data and corresponding graphic.

In the above referenced embodiments, a platform transaction may involve transferring data between the first device or server and a different device or server, where a transaction comprises a digital transaction. A transaction involves a second device that comprises a networked database server or mobile device.

In the above referenced embodiments, the ingested, structured, transformed and transaction data may include industry information and the comparisons of such data that may include any or all of the following types of data: Qualitative or Attribute, to wit: Binomial, Nominal, Ordinal, Interval, Ratio; Quantitative, to wit: Continuous, Discrete; Descriptive; Predictive; Prescriptive; Integer; Floating-point; Character; String; Boolean; Competitive; Financial; Operational; Geographic; Clinical; Molecular; Socioeconomic; Military; Logistics; Experiment: control and intervention; Legal.

In the above referenced embodiments, a networked database server may be configured to store and retrieve at least one of the following types of data as a function of the descriptor: Qualitative or Attribute, to wit: Binomial, Nominal, Ordinal, Interval, Ratio; Quantitative, to wit: Continuous, Discrete; Descriptive; Predictive; Prescriptive; Integer; Floating-point; Character; String; Boolean; Competitive; Financial; Operational; Geographic; Clinical; Molecular; Socioeconomic; Military; Logistics; Experiment: control and intervention; Legal; Library of analytical graphs (e.g. bar, line, scatterplot, waterfall, circle, pie, histogram, gauge, and area graphs).

BRIEF DESCRIPTION OF THE DRAWINGS

The foregoing and other objects, features, and advantages of the invention are apparent from the following detailed description taken in conjunction with the accompanying drawings in which like parts are given like reference numerals and, wherein.

Figure 1:
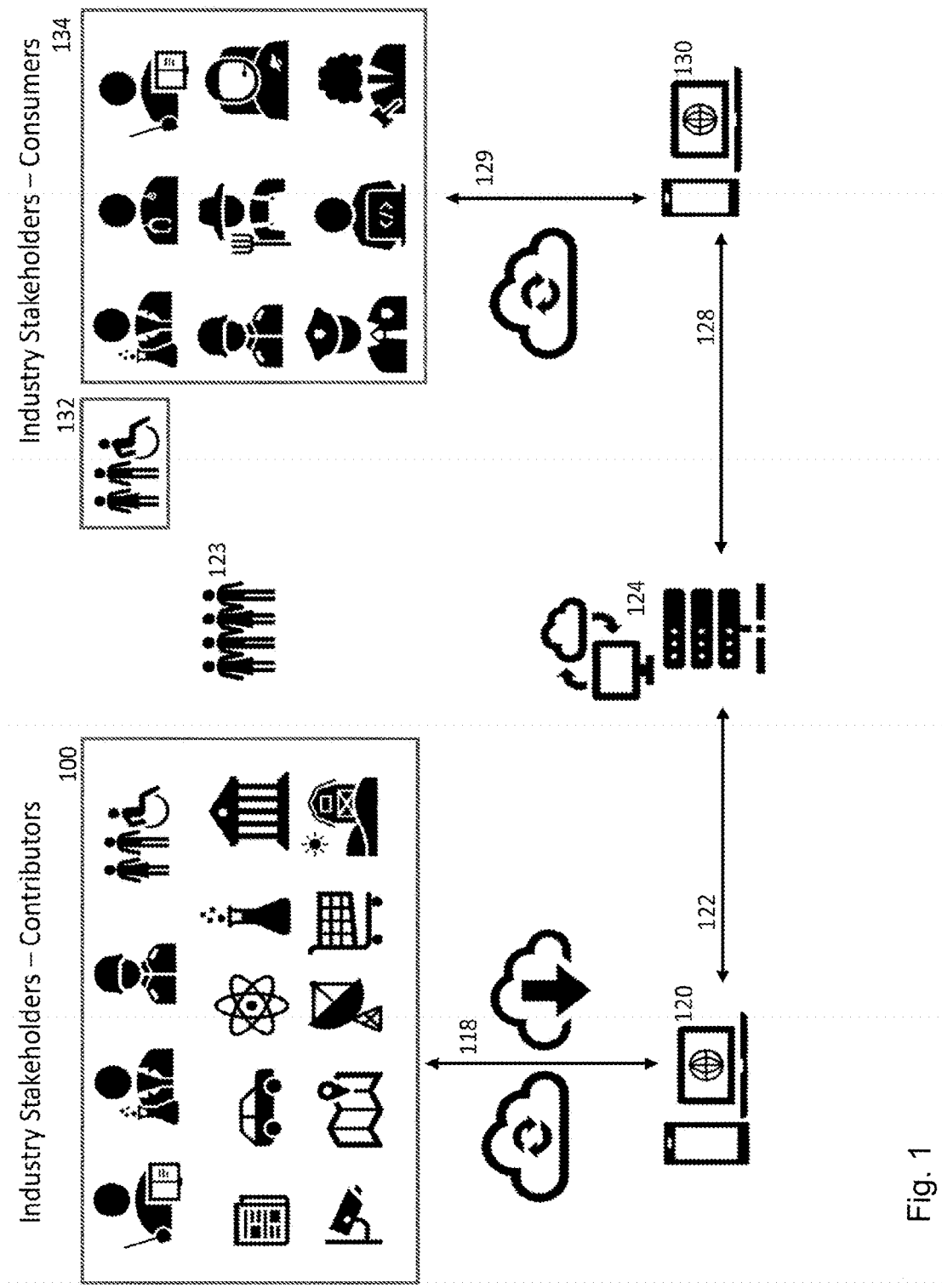
FIG. 1 Contributors of information and consumers of information use a web-based platform to send and receive information.

The images in the drawings are simplified for illustrative purposes and are not depicted to scale. Within the descriptions of the figures, similar elements are provided similar names and reference numerals as those of the previous figure(s). The specific numerals assigned to the elements are provided solely to aid in the description and are not meant to imply any limitations (structural or functional) on the invention.

The appended drawings illustrate exemplary configurations of the invention and, as such, should not be considered as limiting the scope of the invention that may admit to other equally effective configurations. It is contemplated that features of one configuration may be beneficially incorporated in other configurations without further recitation.

DETAILED DESCRIPTION

The FIG. 1 illustrates groups of contributors 100 and industry consumers 132, 134, interacting 118, 122, 128, 129 with their own device 120, 130 via internet on the Innovation company's 123 web-based platform 124. These Contributors create a body of knowledge when they publish content, send data or images, conduct business, communicate 118 through computers or devices 120. All the data 118 can be ingested and sorted into a domain.

Figure 2:
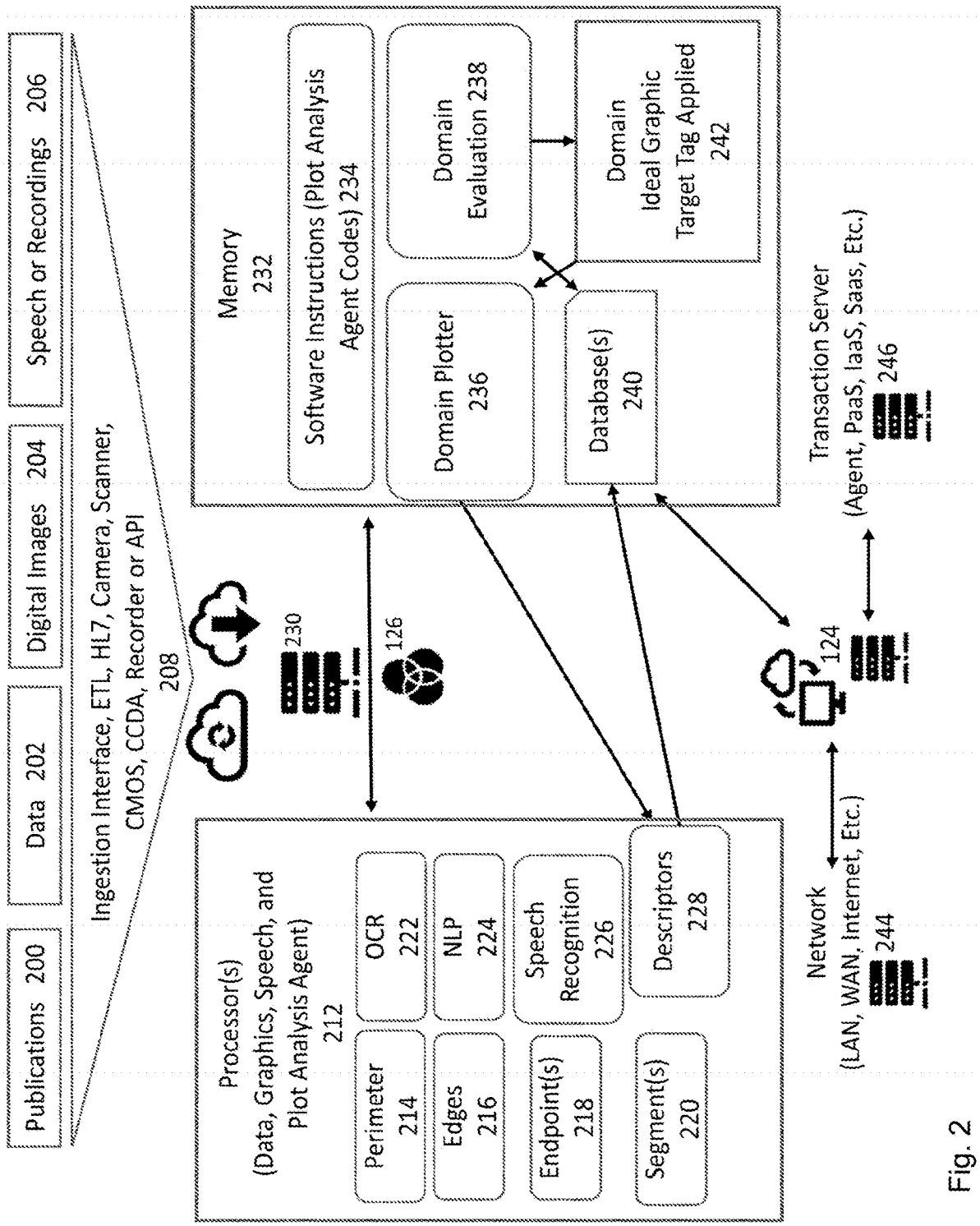
FIG. 2 A server ingests many types of data and graphics through interfaces, then organizes and categorizes ingested data by using memory and processors for output from the database to web-based solutions.

FIG. 2 illustrates publications 200, data 202, digital images 204, speech or voice recordings ingested through means of interfaces, HL7, camera, scanner, Continuity of Care Documents, recorder or APIs 208 in the company 123 server or device 230.

Ingested data is evaluated by server/device 230 memory 232 and processors 212. The server 230 includes processors 212 and memory 232 including software 126, 234 to execute instructions. The term digital image 204 may refer to geologic, topographic, GPS, CT, MRI, PET scans, or analytic graphics of any kind. Each piece of data, including graphics, are evaluated 238 and tagged 242 as belonging to a specific domain. Domain specific information is plotted into a new shape 236 based on software instructions 234 and descriptors 228. All evaluated, tagged and transformed data is stored in the database 240 for use by platform users via connection of their own device 120, 130 to company server/device 124. The illustration does not adequately express the time component of freshness of data ingestion. As referenced herein, data may mean unique data, processed data (e.g. NLP or OCR) or graphics. The intention is for the data ingestion to be ongoing and regular to ensure the body of domain data is as real-time as possible. Company server/device may be connected to a network 244 and include connection to a transaction server (246).

Figure 3:
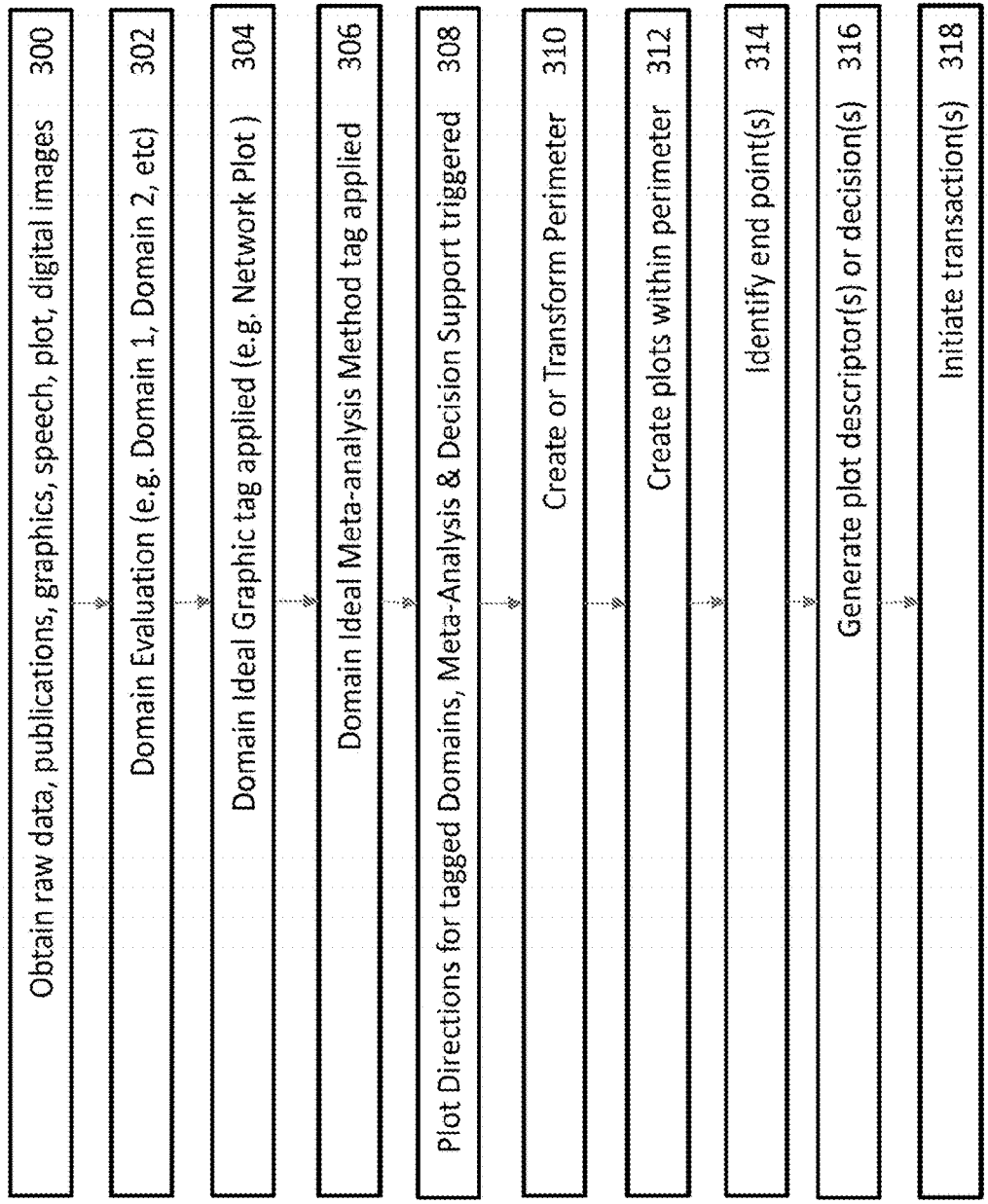
FIG. 3 A text description of the flow of information through the server processes to initiate a transaction.

FIG. 3 describes the contemplated order of operations of data and graphics ingestion 300, evaluating the data 302, assigning an ideal graphic for scenario-specific domain info and meta-analysis ideal graphic 304, for each domain, an ideal meta-analysis method is identified (e.g. regression analysis) and tagged 306, software instructions regarding how to plot the new transformed image representing the domain-specific info is applied 308, the ideal meta-analysis method is also applied and run 308, beginning to create the new ideal shape starts by creating a perimeter 310, plotting data inside the domain-specific shape begins 312, endpoints which represent important piece of data to be displayed in the domain-specific shape are identified 314, new domain-specific shapes are generated and available for prioritized decision making 316. Finally, transactions are initiated by software instructions 318.

In figures, examples of scenario-specific information being transformed is characterized in a new shape, a circle. It is not the intention of this inventive subject matter to be confined to a circle as the best shape for each domain. Depending on the quantity, quality and specificity of some domains, other non-circle shapes may be optimal. For example, an overall industry graphic is discussed and illustrated beginning in FIG. 7. The perimeter of the rectangle includes scenario-specific information. The interior of the rectangle represents how the scenario compares against the known universe across several relevant variables.

Figure 4:
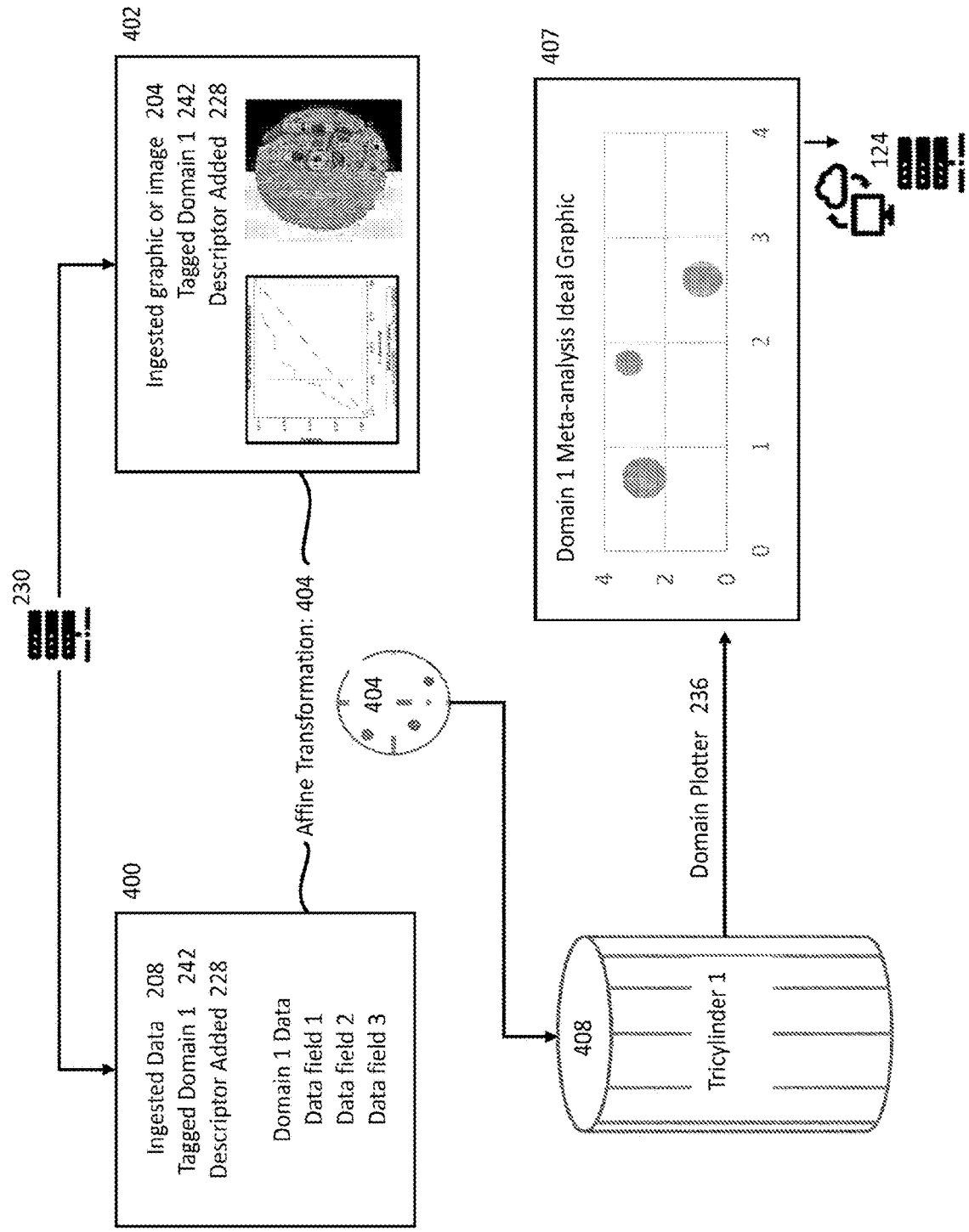
FIG. 4 Data and graphics categorized as Domain 1 are received and transformed to a visual shape which is stored in a virtual domain-specific domain area then plotted on a graphic (shape).

FIG. 4 illustrates the first of the domains (e.g. Domain 1) presented in this inventive material. There are several kinds of data that may be ingested. These include unique data fields, parsed data from articles resulting in unique data fields. Graphics or charts from test results or published articles are ingested. There is more than one type of visual transformation of domain data or graphic. If the data is scenario-specific, a new standardized shape is created 404 with data plotted within the perimeter to represent an individual current status related to the domain. For a healthcare example, diagnosis, stage, setting, co-morbid conditions, symptoms (including history), side effects and status, current treatment and treatment history with any outcomes, status of disease(s) are all plotted in the scenario-specific transformed shape. For non-individual scenario-specific data, a new standardized shape is also created 404, but may not include all the same data points as an individual scenario-specific shape. For example, common scenario-specific data may be a published study regarding experimental results, which includes only outcomes for an uncommon strategy for a rare scenario, meaning the created shape for the common scenario would not include a history plot. Scenario-specific and publication data, graphics and new shapes are stored in the domain-specific area, referred to, for ease of concept, as a cylinder 408. In FIG. 4, all Domain 1 scenario-specific and broader, domain-specific information is stored together in the Domain 1 Tricylinder 408. From this Tricylinder, which includes all Domain 1 information (e.g. historical), an ideal meta-analysis method is run 236 and a new corresponding meta-analysis graphic 407 is created.

Figure 5:
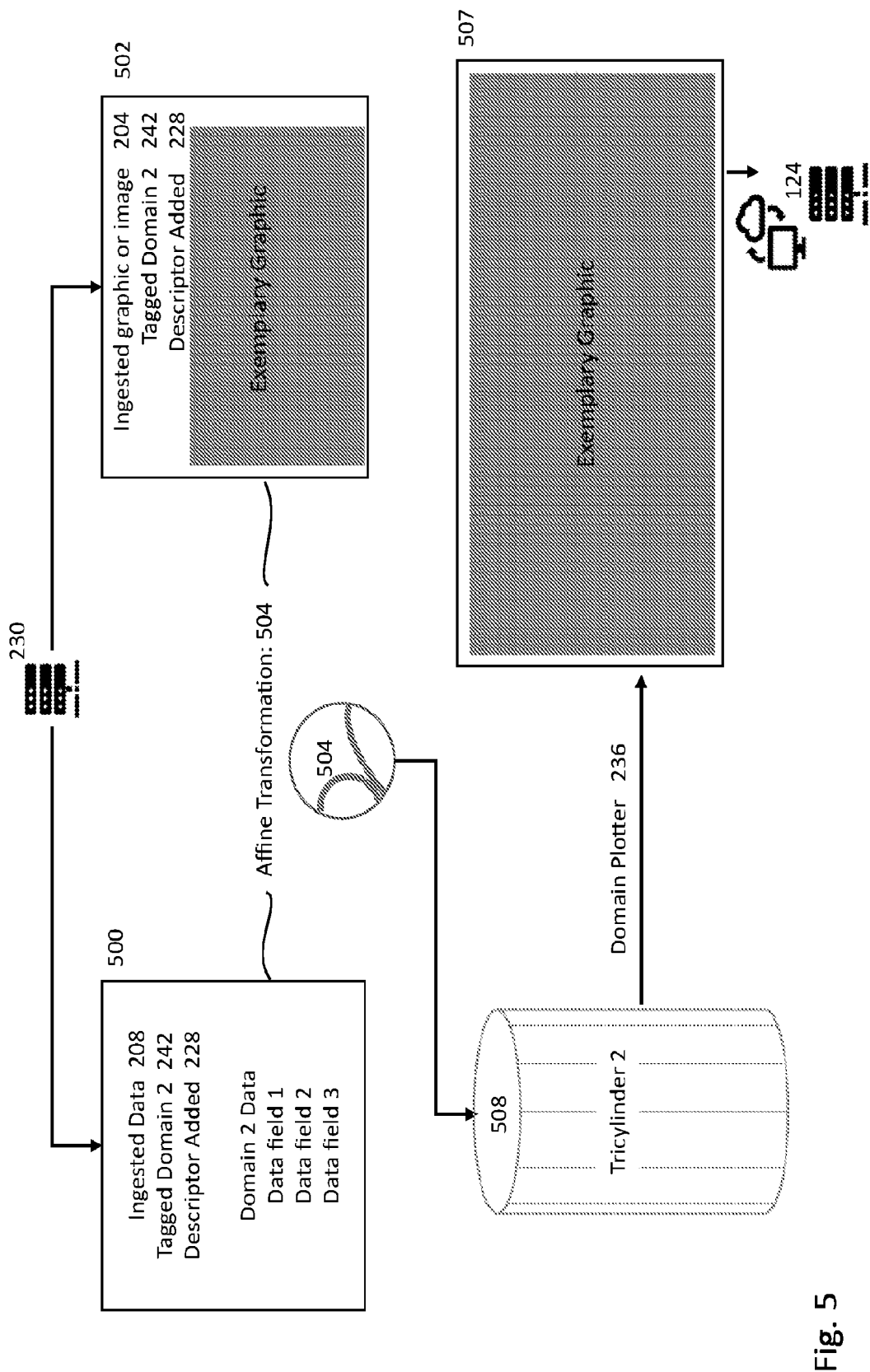
FIG. 5 Data and graphics categorized as Domain 2 are received and transformed to a visual shape which is stored in a virtual domain-specific domain area then plotted on a graphic (shape).

FIG. 5 Similar to above, FIG. 4 illustrates another domain (e.g. Domain 2) presented in this inventive material. In this domain, the data and images that may be ingested are for sophisticated scientific results. Individual or scenario-specific data points may include data from industry knowledge bases for up-to-date information on new or relevant discoveries. All Domain 2—specific information is stored together in the Domain 2 Tricylinder 508. From the Domain 2 Tricylinder, which includes all scientific information, an ideal meta-analysis method is run 236 and a new corresponding meta-analysis graphic 507 is created.

Figure 6:
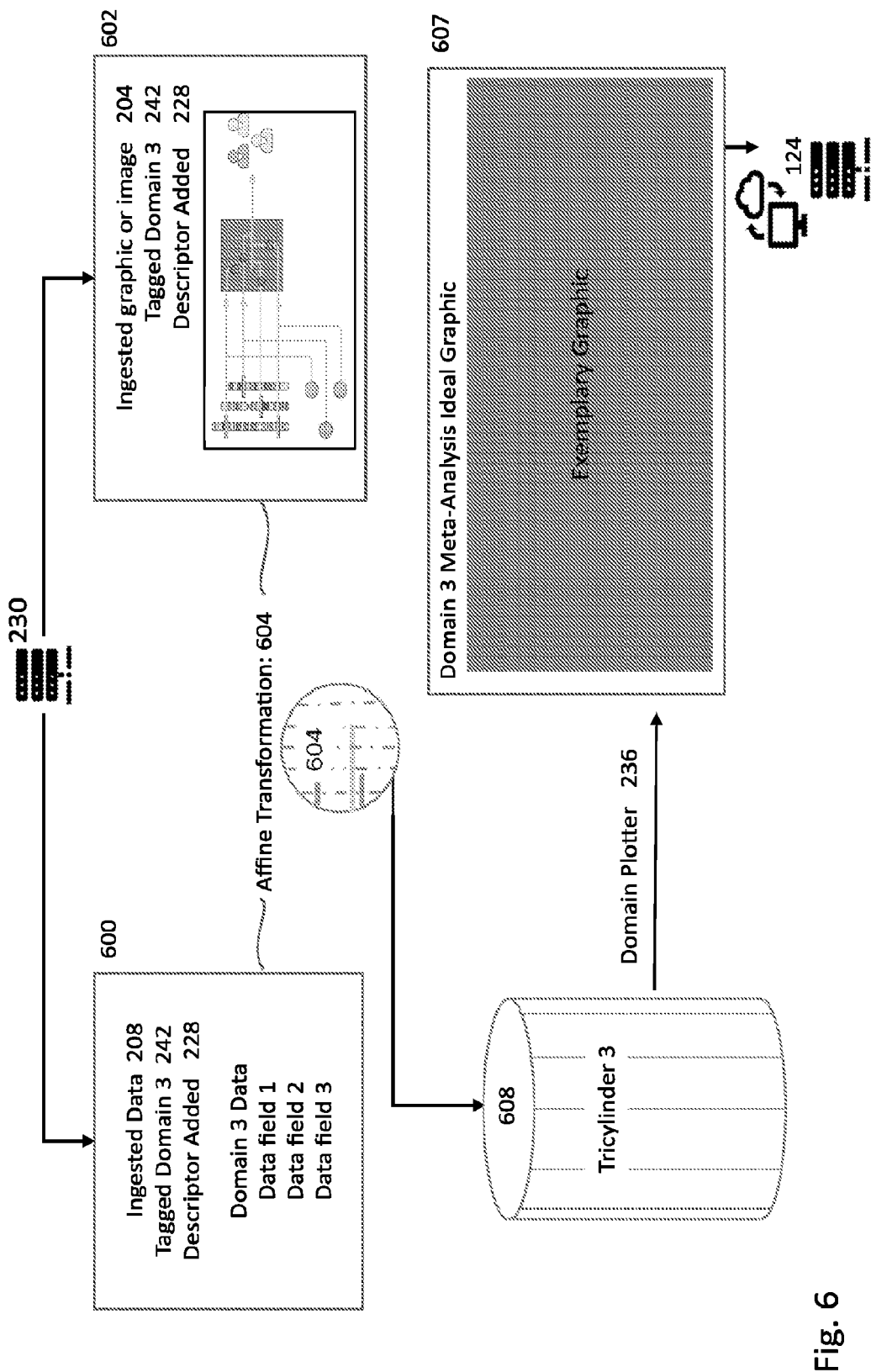
FIG. 6 Data and graphics categorized as Domain 3 are received and transformed to a visual shape which is stored in a virtual domain-specific domain area then plotted on a graphic (shape).

FIG. 6 This figure illustrates the third of the contemplated domains, socioeconomic. There are several kinds of socioeconomic data that may be ingested. These include unique data fields, parsed data from contracts, financial documents, social impact reports resulting in unique data fields. Related graphics or charts from published articles are ingested, tagged and assigned to this domain. This domain includes environmental impact studies, automotive safety databases, social determinants of health including risk factors, poverty and education correlations. For domain-specific data, a new standardized shape is also created 604, but may not include all the same data points as a scenario-specific shape. All socioeconomic domain specific and scenario-specific information is stored together in the Socioeconomic Tricylinder 608. From the Socioeconomic Tricylinder, which includes all Domain 3 information, an ideal Socioeconomic meta-analysis method is run 236 and a new corresponding meta-analysis graphic 607 is created.

Figure 7:
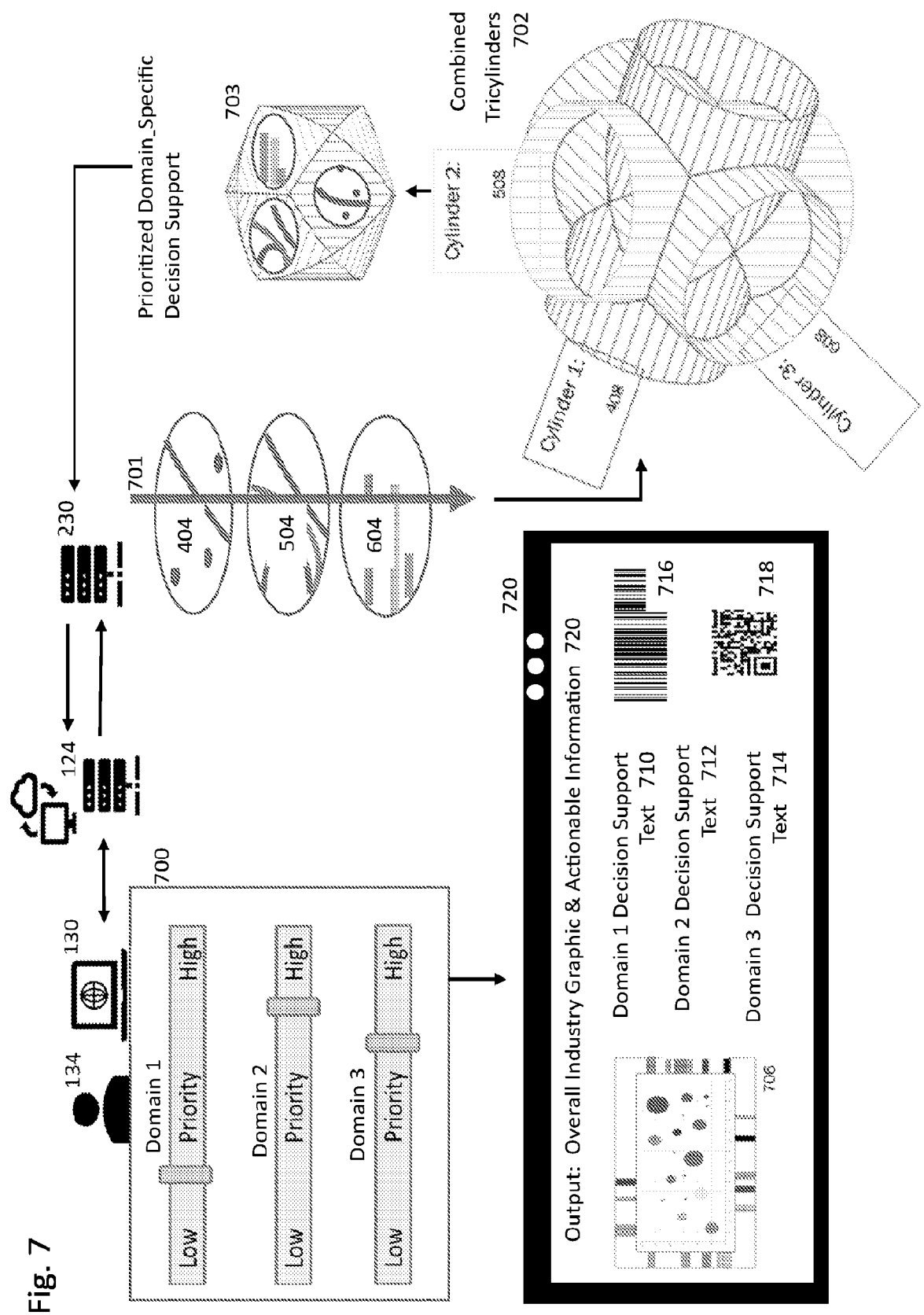
FIG. 7 User prioritizes domain data which initiates machine vision, in context with all domains resulting in a prioritized decision support list and graphic.

FIG. 7 illustrates a user interacting with software to prioritize domain information 700 in order to make a decision. The user prioritizes a domain with relevant information using a mechanism to weight each domain relative to each other. The company server/device 230 adjusts the relative weight of each domain graphic based on user's prioritization. Using company server/device 230, machine vision evaluates weighted graphics in context with each other 701. The multiple domain cylinders which are full of real-time data and meta-analyses are combined in a methodology analogous to the Steinmetz Plot 702. The result of machine vision 701 and combined tricylinders with domain data 702 is a prioritized, multi-domain decision support result 703. The result 720 includes text 710, 712, 714 and graphics 706, 716, 718 displayed for the user 134 on their own device/server 130 connected to company web-based server 124. Note the user may generate as many scenarios as desired as an exercise in hypotheses comparison by weighting domains in various ways to evaluate the outcomes.

Figure 8:
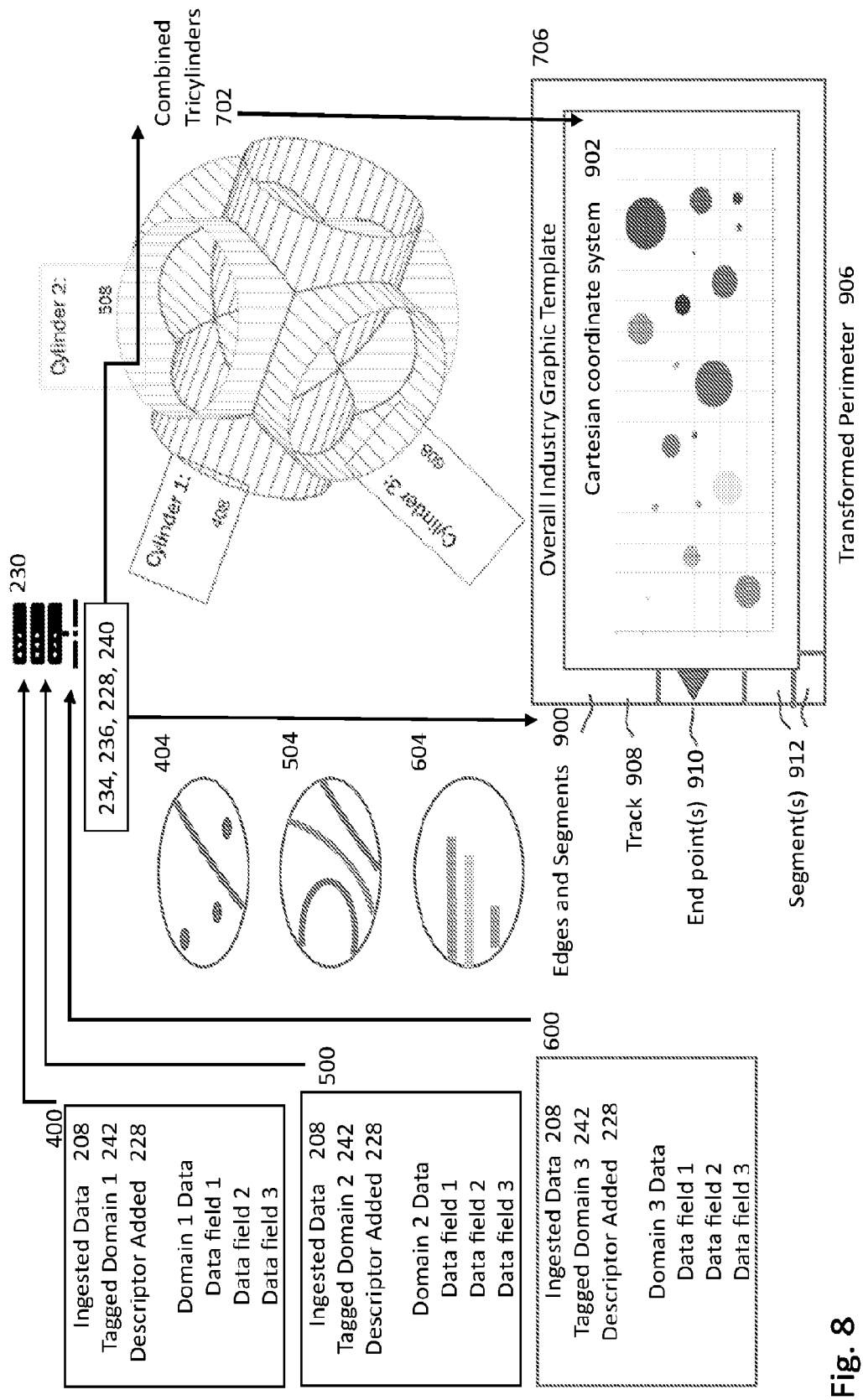
FIG. 8 Data across domains with respective transformed graphic representation of domain is combined to form a new visual providing both an individual scenario and a relative position to broader data.

FIG. 8 Illustrates company server/device 230 utilizing aggregated ingested data from all domains 400, 500, 600 and graphic representations of the domains 404, 504, 604 to create an Overall Graphic 706 using the perimeter of a rectangle to assign important components of each domain. The perimeter is used to define a situation specific or individual characteristics along edges and segments of the rectangle 900, where each domain's unique data is plotted in a track 908, with a specific endpoint related to the data being plotted 910, where the perimeter is broken into segments 912, where domain specific data points are plotted. The perimeter of the Overall Graphic 706 is transformed 906 by plotting all scenario-specific or individual data points from each domain in segments with specific locations allocated to certain data points. Alternatively, the interior of the rectangle 902 is the relative position of this individual, individual scenario compared to the known universe of domain data. The placement of shapes in the interior of the Overall Graphic has meaning, including size, position, and color.

Figure 9:
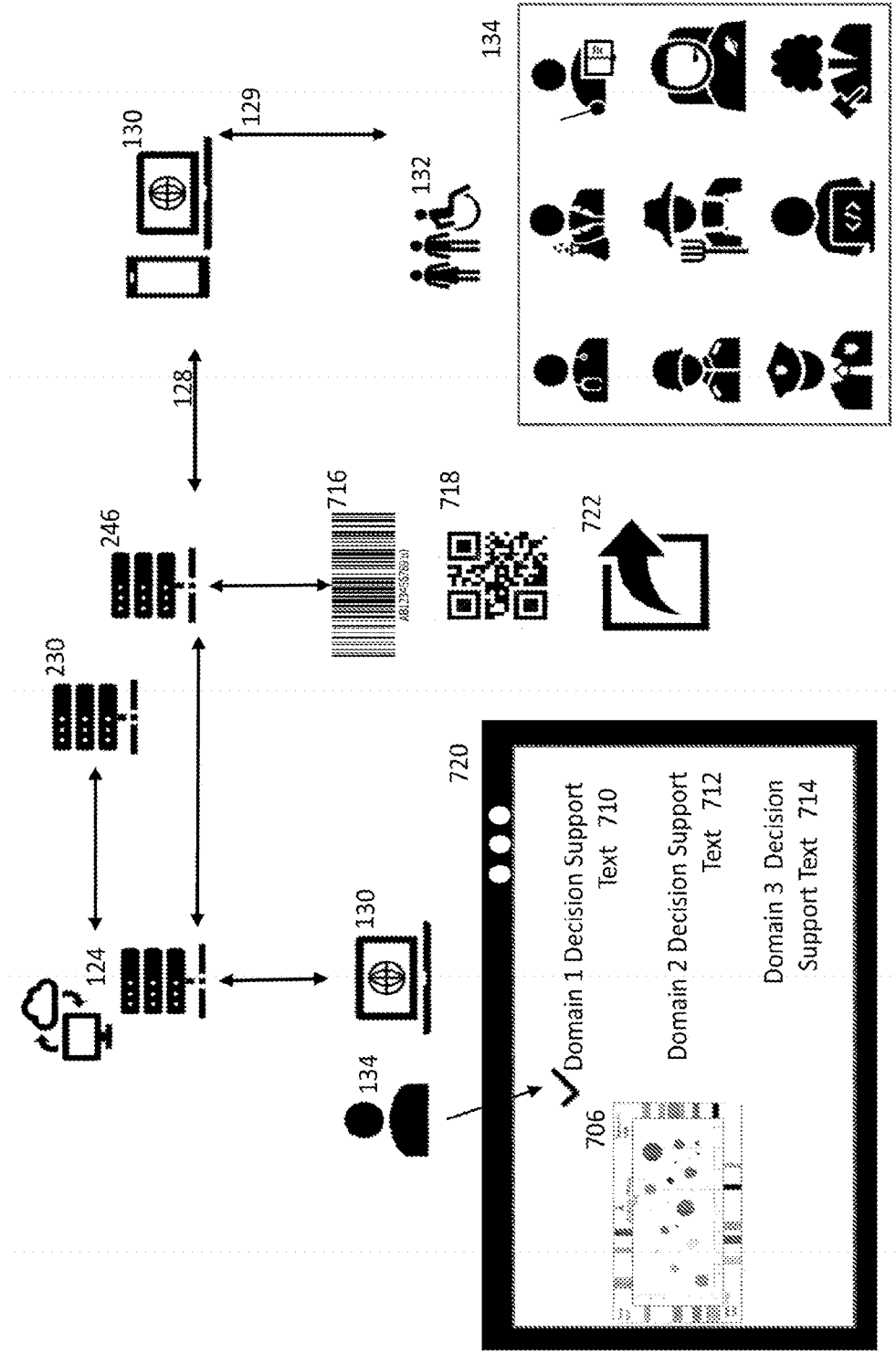
FIG. 9 Bar codes and QR codes, along with other workflow automations are triggered by user's decision support selections.

FIG. 9 illustrates a user 134 interacting with a user interface page from the connected server/device. The user endorses an action to take from the Domain Decision Support text options 710, 712, 714. The user may use the Overall Graphic as a guide to make the decision based on how the individual scenario is presented. The company transaction server 246 converts the decision support items endorsed into portable, useable graphics (e.g. bar code 716 or QR code 718). Additional workflow automation may also be triggered 722. Consumer may interact with any or all of the output from the decision-maker 134 selections from the options 720 and resulting workflow automations 722 or actionable graphics 716, 718.

Figure 10:
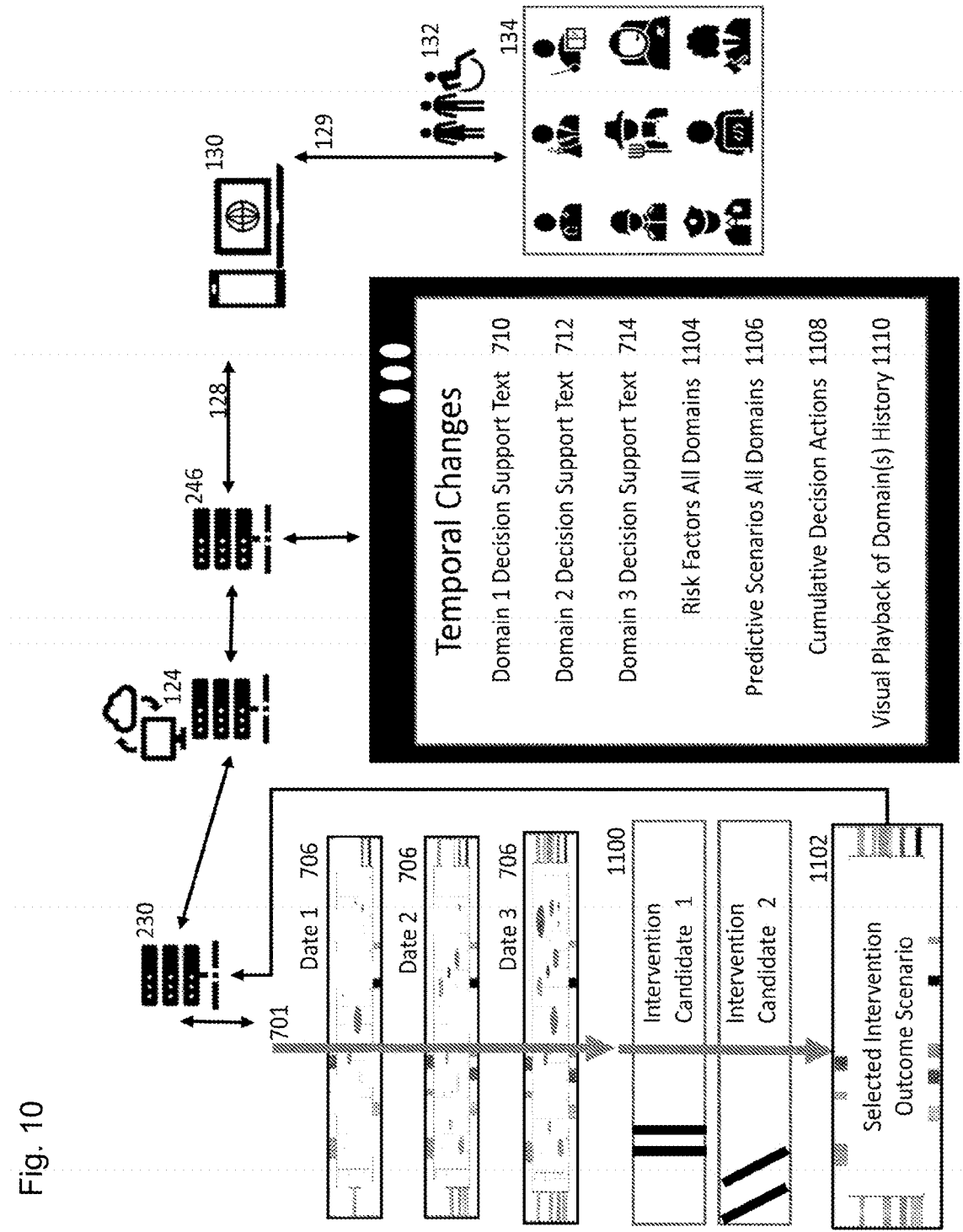
FIG. 10 The evaluation by machine vision of scenario or overall graphics over time may be used to model intervention candidates resulting in a scenario outcome. Additional text and workflow automations are triggered for benefit of users.

FIG. 10 illustrates company server 230 manipulating Overall Graphics from various timepoints which have a specific scenario, situation, or status at each timepoint, in any given range 706 by timepoint. Machine vision 701 is executed to read the stack of Overall Graphics. The capability to run a machine vision scenario using a proposed intervention (related to any domain) 1100 allows varying scenarios to generate in a Selected Intervention Outcome Scenario Overall Graphic 1102. Users may run the machine vision with one or multiple intervention candidates 1100 in order to optimize the desired outcome in the resulting Outcome Scenario Overall Graphic 1102. In addition to the visual representation of the Outcome, company's transaction server generates a dynamic user interface showing temporal changes across domains or by domain, including additional data including risk factors or industry historical results 1104, predictive scenarios for any or all domains 1106 that will morph or play over time for full view of effect of domain decisions, and a list of cumulative decision and triggering actions. Users 132, 134 have access to these results through their connected devices 130.

Figure 11:
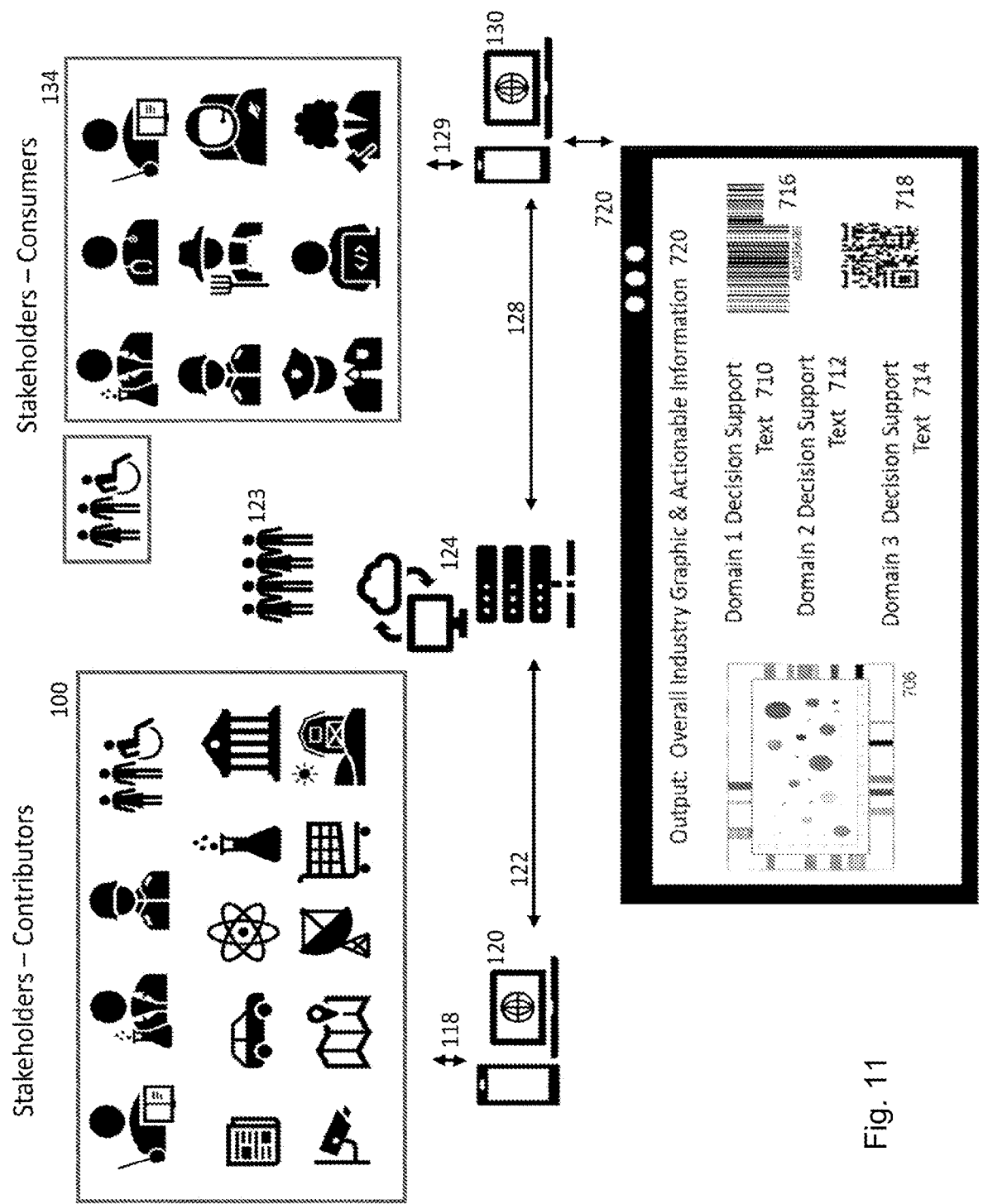
FIG. 11 Summarizes contributors, platform and consumers of information and domain-specific decision support resulting in plots, text and mobile utility graphics.

FIG. 11 In summary, contributors and consumers interact and collaborate on the company's platform 124 to achieve decision-making that is based on real-time data ingested across multiple domains, organized and transformed to graphic representations allowing company's machine vision to provide prioritized domain-specific decision support and overall scenarios for users. Decisions made and resulting outcomes become part of the data in the company database 240 in order that machine vision and outcome scenarios use real-time, real-world evidence. It should be evident that contributors may also become consumers, where the company platform is serving future science, discovery and decision support for those users who initially were contributors only.

The inventive subject matter herein strives to create a methodology, system and workflow automation to allow many domains of information to be combined and analyzed to present the Contributors and Consumers 100, 132, 134 with the broadest, real-time scenario for transactions based on the user's stated priorities. This subject matter intends to combine scientific publications, domain-specific information, business or historical data to use analytics, machine-learning, machine vision to create real-world decision support from across multiple domains which evolves and is modeled over time. Further, it is intended to make such complex information available to all user to make decisions and complex information more portable (e.g. a somatic computer-readable and actionable summary status of all domain-relevant information rather than the information residing across industries, industry-specific software systems or government systems). The invention described herein intends to serve multiple industries, across multiple scenarios, in multiple countries.

An example of a domain-specific scientific information often includes sophisticated graphics to display detail regarding an observation (e.g. a circular plot for a molecular/biologic diagnostic test result). Noteworthy examples of use of Circos (circular plots) are presented in url http://circos.ca/news/scientific_papers/. While the circular plot format is helpful for scientific molecular publications, healthcare industry stakeholders need more human-readable and interpretable graphics to inform decisions. Non-circle graphic plots are generally more appropriate for meta-analysis and subsequent graphic interpretation. Non-circle graphic plots are more human-readable than circle plots.

As a visual tool to help describe the concepts in this inventive material, the Steinmetz Solid is idealized as the solid body obtained at the intersection of two or three cylinders of equal radius at right angles. It is named after mathematician Charles Proteus Steinmetz, who solved the geometric problem of determining the volume of the intersection, though these solids were known long before Steinmetz studied them. The intersection of three cylinders is called a tricylinder, which is used as a visual example herein to assist the reader in understanding the relevance of Domain data, which is sorted into a Cylinder for meta-analysis, graphics display and computation of an Overall Industry or Scenario graphic 720 with decision support 710, 712, 714.

This inventive subject matter will include all relevant meta-analysis methods, both data and graphic outputs to ensure historical research, regardless of analytic or graphic displays in vogue at the time of publication are included appropriately in the ingested data 200, 202, 204, 206.

Many of the figures illustrate a new domain graphic as a circle. Circular plots are typically used to present many layers of detailed information regarding a specific scientific domain to stakeholders. Such plots are incorporated into scientific presentations. However, the circular plots can also be used by one or more healthcare providers (US Patent Publication 20019/0114776, the content and substance of which is incorporated herein by reference) Some Consumers 132, 134 find circular plots on molecular diagnostic test results unintelligible, uninterpretable and therefore not human-readable. Ordinary consumers lack the ability to compare one circular plot to other circular plots in order to make detailed comparisons relating to domain decisions. The designs herein will improve upon traditional circular graphs in all domains, especially as machine vision is enacted.

In order for the envisioned platform to serve users, it requires the combination of massive amounts of various types data and wide-ranging visual graphic presentations of industry information, including experiment results, meta-analysis, historical results. All the data will be required to discover similarities or correlations in domains, initiate hypothesis generation of the combination of some or all of the domains.

Data analysis and meta-analysis mechanisms exist to combine datasets from various collection methods. For example, the oil and gas industry uses data and images regarding surface topography, subsurface geology, and reservoir characteristics.

Proximity to existing and planned surface uses or resources are also significant factors. The very expensive selection of drill sites is also impacted by the terms of the oil and gas lease covering a tract of land. This complex and changing data includes the right to utilize the surface for exploration, drilling and development operations. Additional government regulations create an important domain-specific data set. Regulations require that good faith negotiations with the surface owner take place. If the property is subject to a surface use agreement, the title document should reflect that contractual obligation, legal documents being another example of a domain.

The inventive material is designed to serve many industries. Each industry and each domain has a best-fit model for meta-analysis and ideal graphics which represents existing publications, experiments, and data. By analyzing all available content within domains and presenting the users 100, 132, 134 an intelligent text and graphic representation for decision support 720, decision makers have up-to-date state of the art/science hypotheses. Industry professionals and individual consumers may enjoy improved new drug development, discovery of new oil & gas drilling sites, enhanced security protocols based on historical and real-time data, models for avoiding pandemic damage, new logistic models for just in time materials, measurable cost/value outcomes and improved environmental outcomes.

Regarding the machine vision, it is possible to leverage existing image recognition technologies that could "recognize" an image among many plots. However, the sophistication of the platform requires the combination of existing technologies with custom-made visual parsers and readers.

The above-mentioned Tricylinder can help describe a visual computing approach to evaluate data and graphics in each and across Context-Specific Domains in real-time, ensuring as new data, articles, graphics are created, published, or ingested, they are immediately added to the appropriate domain cylinder. Imagine meta-analysis domain cylinders; all in an ever-changing knowledgebase upon which decision support scenarios are run. An example of the utility of up-to-date, real-world data and graphics is the recent Corona-19 pandemic. Had this platform been in existence prior to 2020, the contributors of the world's data regarding several domains: emergency supplies, hospital capacity models, risk factors, logistic capabilities and appropriate comparator models of SARS or MERS historical data would already have been available for consumer users to model various interventions and model outcomes, triggering automated workflows as needed. Automated workflows may include techniques such as those employed for reading bar codes yield exact interpretations.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Technical Summary

The inventive subject matter provides apparatus, systems and methods in which one or more computing devices are configured to initiate transactions based on a digitally observed domain. One aspect of the inventive subject matter includes a computing device having a computer readable memory and at least one processor. The computing device may be a mobile device or on-premises computer server or web-based service. The memory may store software instructions that encode a machine executable standardized plot analysis agent. Further, in some embodiments, the memory stores one or more plot definitions that describe potentially observable domain-specific plot types. The processor in the device is configured to operate as the standardized plot analysis agent upon execution of the corresponding software instructions. The standardized plot analysis agent includes multiple functionalities that focus on initiating one or more transactions based on digitally observing a standardized plot, a meta-analysis standardized domain plot.

The agent obtains a digital image of a plot, possibly via an optical sensor (e.g., camera, CMOS, CCD, etc.). In some embodiments the meta-analyses' graphical representation or digital images does not properly align with the ideal standardized plot such that the image of the study graphics or plots are skewed. In such embodiments, the agent is able to digitally transform (e.g., affine transform, stretch, rotate, translate, organize, transform etc.) the image of the non-conforming plot to ensure the image of the standardized plot has a form for further processing.

The agent continues by detecting one or more perimeters of the standardized plot in the analytics software or in a digital image. There could be more than one perimeter, possibly associated with multiple tracks of information. The agent also detects a multitude of edges within a perimeter of the standardized plot. Edge detection techniques can be based on Canny edges, edge descriptors, edge constellation descriptors or other types of edge detection algorithms. The agent leverages the edges to map internal chords, if any, of the plot to endpoints located on the perimeter of the plot. Thus, the agent identifies a set of endpoints distributed around the perimeter as a function of the multitude of edges. The agent then generates one or more plot descriptors from the set of endpoints and/or the multitude of edges. For example, a plot descriptor could comprise a cluster of endpoints where each border of endpoint clusters represents a segment of a track around the perimeter of the plot. With the plot descriptors in hand, the agent is able to initiate one or more electronic transactions by using the descriptors as a command code, an index into a look-up table, a query to a database or other construct.

Various shapes, graphs, features, aspects and advantages of the inventive subject matter will become more apparent from the following detailed description of preferred embodiments, along with the accompanying drawing figures.

The detailed description set forth below in connection with the attached drawings is intended as a description of certain embodiments of an image-based plot or graphics recognition and interpretation and transformation system and is not intended to represent the only forms that may be developed or utilized. The description provides detail regarding functions in connection with the illustrated embodiments. However, there may be same or equivalent structure(s), graphics and transformations and/or functions that may be accomplished by different embodiments that are also intended to be encompassed within the scope of the present disclosure. Any use of relational terms such as first and second, and the like are used primarily to distinguish one entity from another without requiring or implying any actual such relationship or order between the entities.

Any language directed to a computer should be read to include any apposite combination of computing devices, including systems, interfaces, servers, agents, databases, controllers, modules, or engines, or other types of computing devices operating individually or together. It is contemplated that the referenced computing devices contain at least one processor, perhaps with multiple cores, configured to execute software instructions stored on a tangible, non-transitory computer readable storage medium (e.g., hard drive, FPGA, PLA, solid state drive, RAM, flash, ROM, etc.). The software instructions configure or program the computing device to provide the various roles, permissions, facilities, or other functionality as discussed below with respect to the disclosed computing device. The disclosed technologies can be embodied as a computer program product that includes a non-transitory computer readable medium storing the software instructions that causes a processor to execute the disclosed steps associated with implementations of computer-based algorithms, processes, methods, or other instructions. In some of the described embodiments, the various, systems, interfaces, agents, databases, controllers exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

This description and throughout the forthcoming claims, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

The disclosed techniques provide many advantageous technical effects including causing a computing device to take electronic action based on digitally observing a graphic or plot. The device converts digital image data of one or more graphic or plots into plot descriptors, which carry some meaning from the plots. Further, the plot descriptors can then be used as a code to initiate one or more electronic transactions (e.g., machine vision, run an algorithm or set of algorithms against a known set of data, query an available database, generate a domain decision suggestion, draft, send for approval a plan of action, transmit a workflow action to a remote system, update a domain, individual record, initiate a machine learning function, return computed information to databases, etc.).

The inventive subject matter is to describe construction or configuration of a computing device to intake, recognize, manipulate, model, hypothesize on complex data including non-digital or digital data, graphics or plots which are not human readable data either alone or in combination with each other. The created computer models and graphic transformations in the memory of the computing devices, could provide greatly enhance a user's understanding of dense domain-specific content which has been constantly updated and calculated through meta-analysis to provide current and useful information and workflow automation to a user of the computing device that the user would lack without such a tool.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Additionally, the number of cylinders described herein, is not intended to limit the number of context-specific domain cylinders possible.

The term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by an embodiment. In some embodiments, the numerical parameters should be construed considering the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all groups used in the forthcoming claims.

An Innovation Company 123 operates a technology platform on a cloud, server, computer, appliance, device 124 receiving input via interface, data entry, graphic recognition, OCR, NLP, voice recognition, source data 122. The Innovation Company receives the data into the computers 123 and leverages electronic recognition of a data, text or image(s) to sort information into Context-Specific Domains 126 to be computed including analyzed, arranged, combined, improved, including meta-analysis, and graphics. The output of the sorted data from 126 exists on Cloud or Computer 124 and may be transmitted 122 to Contributors 100 or Consumers 132, 134 which includes but is not limited to academic researchers, government administrators, educators, scientists, computer/software engineers, judicial and public servants, exploration entities, automotive, or agriculture stakeholders who consume content 129 from their computers, servers or devices 130.

Innovation Company 123 information prepared and delivered 122 to Contributors' computers or devices 120 and delivered 128 to Consumers 132, 134, computers or devices 130 may be described as transactions 129 and involve all user queries from entire body of information 126 via access to cloud, computer 124.

Such Users 100, 132, 134 may refine, sort, arrange, download information 118, 129 via industry transactions or queries from entire body of context-specific domains 126. Domain meta-analyses may be combined (e.g. Domain 1, Domain 2, etc.) 126 which may inform individual decisions or aggregate scenario or business decisions.

The Innovation Company 123 may download publicly available information to cloud computer, server 124 per U.S. Pat. No. 8,719,376B2, the content and substance of which is incorporated herein by reference, Remote Download of Content by inventors Ameesh Palej a et al.

In addition to information publicly available, information may be made available by direct interface 118 to computer or device 120. For example, FHIR is © and ® HL7. The right to maintain FHIR remains vested in HL7 and allows derivative specifications or implementation-related products and services per the HL7 license described at url https://www.hl7.org/fhir/license.html. It is important to note the interfaces or means of data acquisition may vary through allowable mechanisms through licenses or any manner of data entry.

Server, computer, appliance, device receiving input 124 will do so via interface, data entry, or graphic recognition which is noted in U.S. Pat. No. 6,763,148B1, the content and substance of which is incorporated herein by reference, "Image recognition methods" to Inventors Stanley R. Sternberg, et al; Optical Character Recognition (OCR) as in U.S. Pat. No. 8,249,399B2, the content and substance of which is incorporated herein by reference, Optical character recognition verification to Inventors Ella Barkan, et al; Natural Language Processing, voice recognition as in U.S. Pat. No. 5,068,900A, the content and substance of which is incorporated herein by reference, by Inventor Gus Searcy et al; or Direct Ingest of source data per U.S. Pat. No. 8,195,646B2, the content and substance of which is incorporated herein by reference, Systems, methods, and user interfaces for storing, searching, navigating; and retrieving electronic information by Inventor Christopher A. Evans et al 122, 124.

As explained above, stakeholders 100, 132, 134 currently attempt to read, consume and/or summarize research, historical outcomes, new discovery methods, individual-reported data, geographic reports, business cases, contract terms, payment models and policy guidelines to optimize domain experiences. These stakeholders access written content, digital content, audio content and summaries of these modalities.

Each piece of content is part of a larger body of Context-Specific Domain information. For example, the ever-growing content regarding unique technology user behavior and decision psychology is extraordinarily complex and difficult to consume, synthesize and understand for a single domain Stakeholder. For example, Google Search for Nuclear and Missile Defense Policy returned 8,950,000 results. The inventive content herein considers examples of strategic, logistic and policy domains 302, however, there are many more domains to investigate, consume, analyze, synthesize for consumers of many kinds.

The inventive content herein will address the need to collect and evaluate many types of complex data to prepare decision options for decision-makers. In complex, multifaceted industries, there are multiple decisions to make for industry specific roles. Additionally, as part of domain decision calculations 700 each domain may have a priority ranking. A customized method, technology tool based on data collected 208 would provide benefit to contributors and consumers.

The server 230 interfaces with a camera 208, which may be built in devices like represented 120 of FIG. 1. Alternatively, the camera 208 may be entirely separate and not accessible by the device 230, with the device 230 simply receiving image data captured by the camera 208 via removable media or a wired or wireless connection and storing it in memory according to one or more image formats (e.g., as jpg, png, bmp, etc.). The server 230 is comprised of components including, but not limited to processors and agents 212 for data 228, graphics 214, 216, 218, 220, speech 226, and plot analysis 228 and memory 226. The memory 232 includes, but is not limited to software instructions (data, graphics, speech, plot and analysis) agent codes 234. As part of the operation of the software agent codes 234, ingested information 200, 202, 204, 206 is evaluated 238, 240, the relevant ingested information is assigned a domain identifier 242, 240 an ideal graphic tag 242, an ideal meta-analysis tag 242, 240 the tagged information 200, 202, 204, 206 is plotted 236 using domain tag identifier 242 and an ideal graphic representation tag 242, 240 and appropriate meta-analysis methodology tag 242, all done in concert between 238, 236, 240, 242. A database 240 with rules for domain evaluation is available to use descriptors 228 in a learning loop with a network 244 and transaction server 246. The database 240 serves the Context-Specific Domain ideal graphic, meta-analysis methodology and descriptors tag coder 242. Tags 242, plotters 236 and descriptors 228 may all be updated or changed based on new types of information or content 200, 202, 204, 206 being ingested 208 into a server 230 based on new information from models calculated for best data-handling for domain information 240, 244, 246.

The body of knowledge/data 200, 202, 204, 206 is analyzed by an Analysis Agent 212. The server's 230 processor(s) 212 analyzes all data, graphics, and speech. The resulting output 228 may contain detailed information about individual types of publications 200, data 202, digital images 204 or speech 206. Domain information is communicated through the network 244 through server 124 and transmitted to a transaction server 246. All the domain data is tagged for ideal meta-analysis methodology 240, 242, along with an ideal graphic representation suggestion 240, 242. The domain data is processed by meta-analysis 126. The meta-analysis results 126 are then plotted 236 into the ideal graphic format to best explain the findings of the meta-analysis. The sorted, organizes, processed and meta-analyzed data with corresponding ideal graphic applied is made available to the server 124, network 244 and transaction server 246, where users may consume the results as Platform as a Service (PaaS), Software as a Service (Saas), Infrastructure as a Service (IaaS), or direct interface.

Initiating the transaction 406 for the first domain may include referencing a local database 240 stored in the memory 232 or one or more of a remote transaction server 246 via a network 244. The database 240 or transaction server 246 may include a multiple data types tagged according to the same type domain template as is used to generate the domain plot descriptor 236. This process is the same for other domains.

FIG. 5 illustrates two types of ingested data: Data 500 and Digital Images which may include scanned documents, OCR, analytics, charts and graphs 502. Both types of ingested data are transformed (affine transformation 504) by interpreting data and visuals then standardizing into segmented shapes 504. The standardized shape becomes a component input for decision making process 700. The data is evaluated and assigned a domain and associated tag. The tagged data is assigned an ideal meta-analysis methodology and a meta-analysis executed 504 on the ingested data. The meta-analysis includes all related domain data from the database 240. A software transaction is triggered to plot meta-analyzed data in an ideal graphic format (e.g. chosen for the specific domain) 507. The fitness of the transformed digital image and data 507 can be determined by comparing the perimeter edges of the plot to an idea example in the database 240. The comparison can be performed by measuring the deviation of the transformed image's perimeter's edge to an edge of the ideal domain graphic model. The domain ideal graphic and references represent the current summary of the second "cylinder" of data in the below-referenced model of Tricylinder assessment and processing of meta-analyzed data. All domain data has been meta-analyzed and graphed and is represented in Tricylinder 2 508.

Each Cylinder 408, 508, 608 will include a result of meta-analysis most appropriate for the types of data being analyzed. To collect and meta-analyze the rapidly growing body of knowledge in each domain is not possible without technology.

The post-computing output of the Tricylinder analysis is stored in server 703, where graphic software creates the unique Overall Graphic 706. The Overall Graphic 706 represents an individual dataset or a scenario specific cohort of data, their current status, relevant historical data points, and predictive analytics based on the most up-to-date state of each domain. The Overall Graphic 704 is human-readable with training. Additionally, combining capabilities in plot descriptors and decisions 316, with initiating transaction instructions 318, with post-computing output on server 703 machine vision reads changes in individual Overall Graphics, or on accumulation of all Overall Graphics 706 generated.

Transforming the created Overall graphic 706 and/or the Cylinder recommendations 710, 712, 714 using software instructions 232, 234, 240, 244 and available transformations to bar code 716 and/or QR code 718. The bar code 716 generation may be achieved using computers, devices, appliances 124, 122, 128, 130, 230 software 232, 234, 240, 244 and Bar Code Generation as described in US Pat US20130032634A1, the content and substance of which is incorporated herein by reference, by Inventor Sean McKirdy as a system and method for generating and implementing a barcode is provided, wherein the system includes a data generation device configured to receive data and generate barcode data response to the received data, a barcode generation device, configured to receive the barcode data and generate a barcode responsive to the received barcode data, a display device, configured to display the barcode and a barcode receiving device, configured to receive the barcode and operate in response to the barcode. Likewise, another option for consumers is a QR code 718 which may be more suitable for types of transactions 246 based on US Pat US20170134167A1, the content and substance of which is incorporated herein by reference, by Inventor Paul L Carter entitled Systems and methods for QR code validation.

The processes in 212, memory 232, software 234 will operate with the network 244 and server 246 constantly. Computing in 302, 304, 306, 308, 310, 312, 314, 316 and transactions 318 will continually fill the Domain Cylinders 408, 508, 608 ensuring the most current Domain Cylinders output 408, 508, 608 and the Overall Graphic 706 and recommendations 710, 712, 714 are available on demand for users on computer or device 130 connected to device 124.

The Overall Graphics 706 and decision support data and text 710, 712, 714 may be machine-readable, with appropriate processing on the graphic presented using modification of US PAT WO2013131058A2, the content and substance of which is incorporated herein by reference, Machine-vision system and method for remote quality inspection of a product by Inventor Nathan OOSTENDORP, wherein a machine-vision system for monitoring a quality metric for a product. The system includes a controller configured to receive a digital image from an image acquisition device. The controller is also configured to analyze the digital image using a first machine-vision algorithm to compute a measurement of the product. The system also includes a vision server connected to the controller and configured to compute a quality metric and store the digital image and the measurement in a database storage. The system also includes a remote terminal connected to the vision server and configured to display the digital image and the quality metric on the remote terminal.

The standardized, and orientation dependent 706 colorful box-based plot may be assumed to be computer-readable and now includes real-time Real-World information for decisions. FIG. 10 displays an highly hypothetical example of the Overall Graphic (e.g. in this example a potential oil and gas drilling site) status Track 908 (e.g. land rights, title search results, contracting status) and the interior bubble chart compares target drilling site to the all other similar land tracts in the known universe.

In general, the transactions that the domain plot analysis agent and the Tricylinder plot analysis agent with descriptors which generate Overall graphic with decision support data 710, 712, 714 are diverse and may include, for example, financial transactions including purchases, database queries, theoretical outcome based on selected intervention(s), and other industry transactions, notifications and alerts, event logging, cryptographic transactions, blockchain transactions, security transactions, etc. For example, the descriptor could operate as a cryptographic key to lock or unlock additional content.

In some cases, the Domain plots 408, 508, 608 or the Overall Graphic 706 may be in color. The plot analysis agent executed by the processor 212 may therefore perform the various perimeter detections described throughout this disclosure in multiple color channels (e.g. HSV or RGB channels) and the domain plot definition 236 and combined domains into a cylinder 408, 508, 608 or tricylinder 702 may define aspects of the Overall Graphic plot 706 with reference to color. For example, plots of different colors or size may have different meanings that may be used by the plot analysis agent 234 in generating the descriptor(s) 236, 316, 1000, such as a color code for classifying endpoints as sources or destinations. The descriptor(s) 236, 316, 1000 themselves may also be hue-based, including color information of the Overall Graphic plots connecting the endpoints represented.

The Inventive material herein describes the Steinmetz Solid and the accompanying Tricylinder in regard to the example three (3) Domains. It should be understood, the Tricylinder is not meant to be the limit of the number (3) of cylinders to be combined, analyzed and transformed. By reference, descriptions in the url http://paulbourke.net/geometry/cylinders/accessed March 2020, and incorporating the content and descriptions of the multi-cylinder approach, including but not limited to Tetrahedron (4 cylinders) where cylinders intersect through each vertex and the opposite face (This is the same as cylinders through the opposite vertices of a cube); Cube (6 cylinders), where cylinders intersect through the midpoint of each edge; Dodecahedron (6 cylinders) where cylinders intersect through the midpoint of each face, Dodecahedron (10 cylinders) where cylinders through the vertices. The reader may intuit the theme that as many Domains that are relevant to decisions, the inventive material herein would incorporate and expand the number of cylinders as appropriate, still using the described data collection 118, infrastructure 124, 230, processes and agents 212, 232, database(s) 240, networks 244, transaction servers 246, and compiling 702 the ultimate Overall Graphic 706 with decision support 710, 712, 714.

The specific plot descriptors described throughout this disclosure are only examples. Other descriptors developed in accordance with the principles of the innovations described herein may be equally suitable or more or less suitable depending on the particular type of plot and the particular type of transaction initiated by the plot analysis agent. In this regard, descriptors may be modified or newly created depending on which features of the plot (endpoints, source/destination, track, segment, perimeter(s), color relationships, plot/bubble size, etc.) are most useful for each transaction. It should also be noted that descriptors need not be specific to a particular type of plot or shape but may instead be specific to a class of plots. Thus, descriptors may be plot-level invariant, track-level invariant, track segment-level invariant, etc. Descriptors may be invariant to scale or may vary depending on the zoom level of any plot.

It should be apparent to those skilled in the art that many more modifications besides those already described are possible without departing from the inventive concepts herein. The inventive subject matter, therefore, is not to be restricted except in the spirit of the forthcoming claims. Moreover, in interpreting both the specification and the forthcoming claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A data visualization system comprising:
   a computer-implemented data collection module, wherein said data collection module is operable to collect information from a plurality of sources, said information comprising ingested data;
   a computer-implemented data classification and storage module, wherein said data classification and storage module is operable to sort said ingested data into domain-specific data sets, and is further operable to store each domain-specific data set into a domain-specific database;
   a computer-implemented domain analysis module, wherein said domain analysis module is operable to analyze each domain-specific data set generated by said data classification and storage module and to generate a graphical representation in a location within a three-dimensional space of each domain-specific data set generated by said data classification and storage module;
   a computer-implemented user interface, wherein said user interface is operable to allow a user to provide a prioritization weight for each domain-specific data set generated by said data classification and storage module, each prioritization weight changing the size or location of an associated graphical representation of a domain-specific data set relative to non-associated graphical representation; and
   a computer-implemented multi-domain analysis module, wherein said multi-domain analysis module is operable to apply each said prioritization weight to each graphical representation generated by said domain analysis module, and is further operable to generate an overall graphic which represents each domain-specific data set generated by said data classification and storage module as modified by said prioritization weights, wherein the overall graphic is generated based on the relative size and location of each graphical representation.

2. The system of claim 1, wherein said domain analysis module is operable to identify and apply an ideal meta-analysis routine to each domain-specific data set generated by said data classification and storage module.

3. The system of claim 1, wherein said domain analysis module is operable to utilize machine vision algorithms to analyze each domain-specific data set generated by said data classification and storage module and to generate a graphical representation of each domain-specific data set generated by said data classification and storage module.

4. The system of claim 1, wherein said multi-domain analysis module is further operable to utilize machine vision algorithms to analyze each said graphical representation.

5. The system of claim 1, wherein said multi-domain analysis module is further operable to generate and display a human readable overall graphic.

6. The system of claim 1, wherein said data collection module is operable to supplement said ingested data on an ongoing, real time basis, thereby creating updated ingested data; wherein said data classification and storage module is operable to continuously update each domain-specific data set with said updated ingested data, thereby creating an updated domain-specific database; wherein said domain analysis module is operable to continuously update each said graphical representation based on said updated domain-specific database, thereby creating updated graphical representations; and, wherein said multi-domain analysis module is operable to continuously update said overall graphic based on said updated graphical representations.

7. A data visualization system comprising:
a server, said server comprising memory and a processor; and
a network;
wherein said server is connected to said network, and wherein said server is operable to
collect information from a plurality of sources via said network, said information comprising ingested data;
wherein said server is further operable to sort said ingested data into domain-specific data sets, and is further operable to store each domain-specific data set into a domain-specific database;
wherein said server is further operable to analyze each said domain-specific data set and to generate a graphical representation in a location within a three-dimensional space of each said domain-specific data set;
wherein said server is further operable to generate a user interface, wherein said user interface is operable to allow a user to provide a prioritization weight for each said domain-specific data set, each prioritization weight changing the size or location of an associated graphical representation of a domain-specific data set relative to non-associated graphical representations; and
wherein said server is further operable to apply each said prioritization weight to each said graphical representation, and to generate an overall graphic which represents each said domain-specific data set as modified by said prioritization weights, wherein the overall graphic is generated based on the relative size and location of each graphical representation.

8. The system of claim 7, wherein said server is operable to identify and apply an ideal meta-analysis routine to each said domain-specific data set.

9. The system of claim 7, wherein said server is operable to utilize machine vision algorithms to analyze each said domain-specific data set and to generate a graphical representation of each said domain-specific data set.

10. The system of claim 7, wherein said server is further operable to utilize machine vision algorithms to analyze each said graphical representation.

11. The system of claim 7, wherein said server is further operable to generate and display a human readable overall graphic.

12. The system of claim 7, wherein said server is further operable to supplement said ingested data, said domain specific data sets, said graphical representations, and said overall graphic on an ongoing, real time basis.

13. A non-transient computer-readable-medium storing software instructions that cause a processor to perform operations comprising:
collecting information from a plurality of sources, said information comprising ingested data;
sorting said ingested data into domain-specific data sets;
storing each domain-specific data set into a domain-specific database;
analyzing each said domain-specific data set and to generate a graphical representation in a location within a three-dimensional space of each said domain-specific data set;
generating a user interface, wherein said user interface is operable to allow a user to provide a prioritization weight for each said domain-specific data set, each prioritization weight changing the size or location of an associated graphical representation of a domain-specific data set relative to non-associated graphical representations;
applying each said prioritization weight to each said graphical representation; and
generating an overall graphic which represents each said domain-specific data set as modified by said prioritization weights, wherein the overall graphic is generated based on the relative size and location of each graphical representation.

14. The computer-readable-medium of claim 13, wherein said software instructions are operable to cause said processor to identify and apply an ideal meta-analysis routine to each said domain-specific data set.

15. The computer-readable-medium of claim 13, wherein said software instructions are operable to cause said processor to utilize machine vision algorithms to analyze each said domain-specific data set and to generate a graphical representation of each said domain-specific data set.

16. The computer-readable-medium of claim 13, wherein said software instructions are operable to cause said processor to utilize machine vision algorithms to analyze each said graphical representation.

17. The computer-readable-medium of claim 13, wherein said software instructions are operable to cause said processor to generate and display a human readable overall graphic.

18. The computer-readable-medium of claim 13, wherein said software instructions are operable to cause said processor to supplement said ingested data, said domain specific data sets, said graphical representations, and said overall graphic on an ongoing, real time basis.

19. A method of analyzing distinct data sets comprising:
providing a computer system, wherein said computer system comprises a process and memory;
collecting information from a plurality of sources using said computer, said information comprising ingested data;
sorting said ingested data into domain-specific data sets using said computer;
storing each domain-specific data set in a domain-specific database in said memory;
analyzing each said domain-specific data set with said computer and generating a graphical representation in a location within a three-dimensional space of each said domain-specific data set;
generating and displaying a user interface using said computer;
collecting through said user interface a prioritization weight for each said domain-specific data set;
applying each said prioritization weight to each said graphical representation, each prioritization weight changing the size or location of an associated graphical representation of a domain-specific data set relative to non-associated graphical representations; and
generating an overall graphic which represents each said domain-specific data set as modified by said prioritization weights, wherein the overall graphic is generated based on the relative size and location of each graphical representation.

20. The method of claim 19, wherein said sorting step further comprises: identifying and applying an ideal meta-analysis routine to each said domain-specific data set.

21. The method of claim 19, wherein said analyzing step further comprises utilizing machine vision algorithms to analyze each said domain-specific data set and to generate a graphical representation of each said domain-specific data set.

22. The method of claim 19, wherein said step of generating an overall graphic further comprises generating and displaying a human readable overall graphic.

23. The method of claim 19, wherein said steps of collecting information, sorting said ingested data into domain-specific data sets, analyzing each said domain-specific data set, generating a graphical representation of each said domain-specific data set, and generating an overall graphic are continuously repeated in real-time.

* * * * *